(12) United States Patent
Natan et al.

(10) Patent No.: US 9,239,327 B2
(45) Date of Patent: Jan. 19, 2016

(54) PARTICLES COMPRISING HOLLOW SURFACE-ENHANCED SPECTROSCOPY (SES)-ACTIVE CORE FOR LONG WAVELENGTH SERS

(75) Inventors: Michael J. Natan, Los Altos, CA (US); Richard Griffith Freeman, Mountain View, CA (US); Marcelo Eduardo Piotti, Freemont, CA (US); William E. Doering, Santa Clara, CA (US); Felicia Tam, Sunnyvale, CA (US)

(73) Assignee: SICPA Holding SA (CH)

( * ) Notice: Subject to any disclaimer, the term of this patent is extended or adjusted under 35 U.S.C. 154(b) by 1106 days.

(21) Appl. No.: 13/319,648

(22) PCT Filed: May 18, 2010

(86) PCT No.: PCT/US2010/035300
§ 371 (c)(1),
(2), (4) Date: Nov. 9, 2011

(87) PCT Pub. No.: WO2010/135354
PCT Pub. Date: Nov. 25, 2010

(65) Prior Publication Data
US 2012/0057165 A1    Mar. 8, 2012

Related U.S. Application Data

(60) Provisional application No. 61/179,281, filed on May 18, 2009, provisional application No. 61/181,598, filed on May 27, 2009.

(51) Int. Cl.
*G01N 37/00* (2006.01)
*G01N 33/532* (2006.01)
(Continued)

(52) U.S. Cl.
CPC ............ *G01N 33/532* (2013.01); *G01N 21/658* (2013.01); *G01N 33/28* (2013.01)

(58) Field of Classification Search
CPC .............. G01N 21/658; G01N 33/587; G01N 2021/656; G01N 33/553; G01N 2021/655; G01N 2021/653; G01N 21/35; G01N 33/54346; G01N 21/554; G01N 21/47; G01N 33/582; G01N 21/359; G01N 21/553; B82Y 30/00
See application file for complete search history.

(56) References Cited

U.S. PATENT DOCUMENTS

| 6,514,767 B1 | 2/2003 | Natan |
| 6,861,263 B2 | 3/2005 | Natan |

(Continued)

OTHER PUBLICATIONS

Hayes et al., "Core-shell particles: Preparation, fundamentals and applications in high performance liquid chromatography", Journal of Chromatography A, 2014, v. 1357, pp. 36-52.*

(Continued)

*Primary Examiner* — Yelena G Gakh
(74) *Attorney, Agent, or Firm* — Swanson & Bratschun, L.L.C.

(57) ABSTRACT

Embodiments include a particle comprising a surface enhanced spectroscopy (SES)-active core and a SES-active reporter molecule associated with the SES-active core wherein said particle has a measurable SES spectrum when excited by incident light having a wavelength of at least 1400 nm. Alternative embodiments include methods of manufacturing said particle and methods of tagging a material with said particle. The particle may include an SES-active core which supports plasmon resonance at a wavelength of at least 1400 nm. The particle may comprise an anisotropic core. The particle may include an SES-active reporter molecule which is resonant at one or more wavelengths greater than or equal to 1400 nm.

5 Claims, 7 Drawing Sheets

(51) Int. Cl.
G01N 21/65 (2006.01)
G01N 33/28 (2006.01)

(56) References Cited

U.S. PATENT DOCUMENTS 7,443,489 B2 10/2008 Natan
2008/0241262 A1 10/2008 Lee et al.
2008/0305489 A1 12/2008 Thomas et al.

OTHER PUBLICATIONS

Michaels et al., "Ag Nanocrystal Junctions as the Site for Surface-Enhanced Raman Scattering of Single Rhodamine 6G Molecules", J. Phys. Chem. B, 2000, 104, 11965-11971.*
Pavel et al., "Vibrational behavior of transition metal cupferronato complexes. Raman and SERS studies on nickel(II) cupferronato complexes", Vibrat. Spectrosc., 2000, v. 23, pp. 71-76.*
Rubim et al., "Surface-Enhanced Raman Spectroscopic (SERS and FT-SERS) Investigation of the Complex Ion [Fe2(CN)10L]6-(L = 4,4'-Bipyridine and Pyrazine) Adsorbed on Silver and Gold Electrodes", J. Phys. Chem. 1995, v. 99, pp. 345-355.*
Wang et al., "Near-infrared surface-enhanced Raman scattering of a kind of self-assemblies film based on coordination bond", Materials Science & Engineering C (1999) vol. 10, p. 3-6.
Le et al., "Metallic Nanoparticle Arrays: A Common Substrate for Both Sufrace-Enhanced Raman Scattering and Surface-Enhanced Infrared Absorption" ACS Nano (2008) vol. 2 (4), p. 707-714.
International Search Report and Written Opinion mailed Aug. 4, 2010 for corresponding International Patent Application No. PCT/US10/35300.
Adar et al., "Raman Microscopy Extends Frontiers of Biomedical Research", Raman Spectroscopy, Biophotonics International, Mar. 2006, pp. 44-48.
Ah, et al., "Preparation of $Au_{core}Ag_{shell}$ Nanorods and Characterization of Their Surface Plasmon Resonances", The Journal of Physical Chemistry B, vol. 105, No. 33, Aug. 23, 2001, pp. 7871-7873.
Aherne, et al., "Optical Properties and Growth Aspects of Silver Nanoprisms Produced by a Highly Reproducible and Rapid Synthesis at Room Temperature", Advanced Functional Materials, 2008, 18, pp. 2005-2016.
Aizpurua, et al., "Optical properties of coupled metallic nanorods for field-enhanced spectroscopy", Physical Review B 71, 235420, 2005, pp. 1-13.
Alvarez-Puebla, et al., "Surface-Enhanced Raman Scattering on Nanoshells with Tunable Surface Plasmon Resonance", Langmuir, 2005, pp. A-E.
Amendola, et al., "Laser ablation synthesis in solution and size manipulation of noble metal nanoparticles", Physical Chemistry Chemical Physics, 2009, 11, pp. 3805-3821.
Bakr, et al., "High-Yield Synthesis of Multi-Branched Urchin-Like Gold Nanoparticles", Chem. Mater., 2006, vol. 18, No. 14, pp. 3297-3301.
Bardhan, et al., "Nanosphere-in-a-Nanoshell: A Simple Nanomatryushka", J. Phys. Chem. C, 2010, vol. 114, No. 16, pp. 7378-7383.
Brinson, et al., "Nanoshells Made Easy: Improving Au Layer Growth on Nanoparticle Surfaces", Langmuir 2008, 24, pp. 14166-14171.
Chah, et al., "Nanostructured Gold Hollow Microspheres Prepared on Dissolvable Ceramic Hollow Sphere Templates", Journal of Colloid and Interface Science, 2002, 250, pp. 142-148.
Chang, et al., "Hydrothermal Synthesis of Monodispersed Octahedral Gold Nanocrystals with Five Different Size Ranges and Their Self-Assembled Structures", Chem. Mater., 2008, vol. 20, No. 24, pp. 7570-7574.
Chattopadhyay, et al., "Quantum dot semiconductor nanocrystals for immunophenotyping by polychromatic flow cytometry", Nature Medicine, Aug. 2006, vol. 12, No. 8, pp. 972-977.
Chen, et al., "Optical Properties of Pd—Ag and Pt—Ag Nanoboxes Synthesized via Galvanic Replacement Reactions", Nano Letters, 2005, vol. 5, No. 10, pp. 2058-2062.

Cui, et al., "Synthesis of $Ag_{core}Au_{shell}$ Bimetallic Nanoparticles for Immunoassay Based on Surface-Enhanced Raman Spectroscopy", J. Phys. Chem. B, 2006, vol. 110, No. 9, pp. 4002-4006.
Driskell, et al., "Labeled Gold Nanoparticles Immobilized at Smooth Metallic Substrates: Systematic Investigation of Surface Plasmon Resonance and Surface-Enhanced Raman Scattering", J. Phys, Chem. B, 2006, pp. A-H.
Fang, et al., "Aggregation and surface-enhanced Raman activity study of dye-coated mixed silver-gold colloids", Journal of Raman Spectroscopy, 2004, 35, pp. 914-920.
Faulds, et al., "Comparison of Surface-Enhanced Resonance Raman Scattering from Unaggregated and Aggregated Nanoparticles", Anal. Chem., 2004, vol. 76, No. 3, pp. 592-598.
Felidj, et al., "A new approach to determine nanoparticle shape and size distributions of SERS-active gold-silver mixed colloids", 1998, pp. 725-732.
Gellner, et al., "Optical properties and SERS efficiency of tunable gold/silver nanoshells", Vibrational Spectroscopy, 2008.
Genov, et al., "Resonant Field Enhancements from Metal Nanoparticle Arrays", Nano Letters, 2004, vol. 4, No. 1, pp. 153-158.
Gonzalez, et al., "Photochemical Strategies for the Facile Synthesis of Gold-Silver Alloy and Core-Shell Bimetallic Nanoparticles", J. Phys, Chem. C, 2009, vol. 113, No. 27, pp. 11861-11867.
Heitsch, et al., "Colloidal Silicon Nanorod Synthesis", Nano Letters, 2009, vol. 9, No. 8, pp. 3042-3047.
Hirsch, et al., "Metal Nanoshells", Annals of Biomedical Engineering, vol. 34, No. 1, Jan. 2006, pp. 15-22.
Jana, et al., "Seed-Mediated Growth Approach for Shape-Controlled Synthesis of Spheroidal and Rod-like Gold Nanoparticles Using a Surfactant Template", Advanced Materials, 2001, vol. 13, No. 18, pp. 1389-1393.
Jin, et al., "Photoinduced Conversion of Silver Nanospheres to Nanoprisms", Science, Nov. 30, 2001, vol. 294, pp. 1901-1903.
Jin, et al., "Controlling anisotropic nanoparticle growth through Plasmon excitation", Nature, Oct. 2, 2003, vol. 425, pp. 487-490.
Jin, et al., "Spectrally Tunable Leakage-Free Gold Nanocontainers", J. Am. Chem. Soc., 2009, 131, pp. 17774-17776.
Johnson, et al., "Carbonplatin (C) + Paclitaxel (T) + RhuMab-VEGF (AVF) May Prolong Survival in Advanced Non-Squamous Lung Cancer", Proc. Am. Soc. Clin. Oncol., 20, 2001 (abstract 1256).
Joseph, et al., "Surfactant-Directed Multiple Anisotropic Gold Nanostructures: Synthesis and Surface-Enhanced Raman Scattering", Langmuir, 2009, 25 (22), pp. 13224-13231.
Kariuki, et al., "Composition-Controlled Synthesis of Bimetallic Gold-Silver Nanoparticles", Langmuir, 2004, vol. 20, No. 25, pp. 11240-11246.
Kim, et al., "Facile Method to Prepare Surface-Enhanced-Raman-Scattering-Active Ag Nanostructures on Silica Spheres", Langmuir, 2006, vol. 22, No. 19, pp. 8083-8088.
Klein, et al., "Second-Harmonic Generation from Magnetic Metamaterials", Science, Jul. 28, 2006, vol. 313, pp. 502-504.
Kou, et al., "Curvature-Directed Assembly of Gold Nanocubes, Nanobranches, and Nanospheres", Langmuir, 2009, vol. 25, No. 3, 1692-1698.
Lassiter, et al., "Close Encounters between Two Nanoshells", Nano Letters, 2008, pp. A-G.
Le, et al., "Metallic Nanoparticle Arrays: A Common Substrate for Both Surface-Enhanced Raman Scattering and Surface-Enhanced Infrared Absorption", ACSNano, 2008, pp. A-L.
Lee, et al., "Hot Spots in Silver Nanowire Bundles for Surface-Enhanced Raman Spectroscopy", J. Am. Chem. Soc., 2006, vol. 126, No. 7, pp. 2200-2201.
Liang, et al., "High-Yield Uniform Synthesis and Microstructure-Determination of Rice Shaped Silver Nanocrystals", J. Am. Chem. Soc., 2009, vol. 131, No. 17, pp. 6068-6069.
Lim, et al., "Mechanistic Study of the Synthesis of Au Nanotadpoles, Nanokites, and Microplates by Reducing Aqueous $HAuCl_4$ with Poly(vinyl pyrrolidone)", Langmuir, 2008, pp. A-F.
Lim, et al., "Multifunctional Fullerene-Mediated Assembly of Gold Nanoparticles", Chem Mater., 2005, vol. 17, No. 26, pp. 6528-6531.
Lim, et al., "Homocysteine-Mediated Reactivity and Assembly of Gold Nanoparticles", Langmuir, 2006, pp. A-H.

(56) References Cited

OTHER PUBLICATIONS

Lim, et al., "Nanogap-engineerable Raman-active nanodumbbells for single-molecule detection", Nature Materials, Jan. 2010, vol. 9, pp. 60-67.
Link, et al., "Alloy Formation of Gold-Silver Nanoparticles and the Dependency of the Plasmon Absorption on Their Composition", J. Phys. Chem. B, 1999, vol. 103, No. 18, pp. 3529-3533.
Lynn, et al., "Short-wave infrared excited SERS", Analyst, 2010, 135, pp. 1904-1905 (plus supplementary material for Analyst).
Lyvers, et al., "Gold Nanorod Arrays as Plasmonic Cavity Resonators", ACSNano, 2008, vol. 2, No. 12, pp. 2569-2576.
Mallin, et al., "Solution-Phase Synthesis of Sub-10 nm Au—Ag Alloy Nanoparticles", Nano Letters, 2002, vol. 2, No. 11, pp. 1235-1237.
Mandal, et al., "Keggins Ions as UV-Switchable Reducing Agents in the Synthesis of Au Core—Ag Shell Nanoparticles", J. Am. Chem. Soc., 2003, vol. 125, No. 28, pp. 8440-8441.
Martin, et al., "Turning up the Lights—Fabrication of Brighter SERRS Nanotags", Chemical Communications, 2010, 46 (29), pp. 5247-5249.
Millstone, et al., "Observation of a Quadrupole Plasmon Mode for a Colloidal Solution of Gold Nanprisms", J. Am. Chem. Soc., 2005, vol. 127, No. 15, pp. 5312-5313.
Mulvihill, et al., "Anisotropic Etching of Silver Nanoparticles for Plasmonic Structures Capable of Single-Particle SERS", J. Am. Chem.. Soc., 2010, vol. 132, No. 1, pp. 268-274.
Murphy, et al., "Gold Nanoparticles in Biology: Beyond Toxicity to Cellular Imaging", Accounts of Chemical Research, 2008, pp. A-J.
Nakashima, et al., "Self-Assembly of Gold Nanorods Induced by Intermolecular Interactions of Surface-Anchored Lipids", Langmuir, 2008, pp. A-E.
Ni, et al., "Tailoring Longitudinal Surface Plasmon Wavelengths, Scattering and Absorption Cross Sections of Gold Nanorods", ACS nano, 2008, vol. 2, Issue 4, pp. 677-686.
Nie, et al., "'Supramolecular' Assembly of Gold Nanorods End-Terminated with Polymer "Pom-Poms": Effect of Pom-Pom Structure on the Association Modes", J. Am. Chem. Soc., 2008, 130 (11), pp. 3683-3689.
Niu, et al., "Selective Synthesis of Single-Crystalline Rhombic Dodecahedral, Octahedral, and Cubic Gold Nanocrystals", J. Am. Chem. Soc., 2009, 131(2), pp. 697-703.
Norman, et al., "Near Infrared Optical Absorption of Gold Nanoparticle Aggregates", J. Phys. Chem. B, 2002, vol. 106, No. 28, pp. 7005-7012.
Odom, et al., "How Gold Nanoparticles Have Stayed in the Light: The 3 M's Principle", ACS Nano, 2008, vol. 2, No. 4, pp. 612-616.
Okitsu, et al., "One-Pot Synthesis of Gold Nanorods by Ultrasonic Irradiation: The Effect of pH on the Shape of the Gold Nanorods and Nanoparticles", Langmuir, 2009, 25(14), pp. 7786-7790.
Penninkhof, et al., "Optical Properties of Spherical and Oblate Spheroidal Gold Shell Colloids", J. Phys. Chem. C., 2008, pp. A-E.
Pietrobon, et al., "Photochemical Synthesis of Monodisperse Size-Controlled Silver Decahedral Nanoparticles and Their Remarkable Optical Properties", Chem. Mater, 2008, pp. A-E.
Pietrobon, et al., "Synthesis of Size-Controlled Faceted Pentagonal Silver Nanorods with Tunable Plasmonic Properties and Self-Assembly of These Nanorods", ACS Nano, 2009, 3(1), pp. 21-26.
Preston, et al., "Preparation and Optical Properties of Metallodielectric Core-Shell-Corona Particles", J. Phys. Chem. C, 2008, pp. A-E.
Ribou, et al., "Intervalence Electron Transfer in Mixed Valence Diferrocenylpolyenes. Decay Law of the Metal-Metal Coupling with Distance", Inorg. Chem., 1996, vol. 35, No. 13, pp. 3735-3740.
Rodriguez-Fernandez, et al., "Spectroscopy, Imaging, and Modeling of Individual Gold Decahedra", J. Phys, Chem. C., 2009, pp. A-I.
Schwartzberg, et al., "Unique Gold Nanoparticle Aggregates as a Highly Active Surface-Enhanced Raman Scattering Substrate", J. Phys. Chem. B, 2004, vol. 108, No. 50, pp. 19191-19197.
Schwartzberg, et al., "Improving Nanoprobes Using Surface-Enhanced Raman Scattering from 30-nm Hollow Gold Particles", Anal. Chem., 2006, vol. 78, No. 13, pp. 4732-4736.
Schwartzberg, et al., "Novel Optical Properties and Emerging Applications of Metal Nanostructures", J. Phys. Chem., 2008, pp. A-N.
Seo, et al., "Ag—Au—Ag Heterometallic Nanorods Formed through Directed Anisotropic Growth", J. Am. Chem. Soc., 2008, pp. A-B.
Shanmukh, et al., "Rapid and Sensitive Detection of Respiratory Virus Molecular Signatures Using a Silver Nanorod Array SERS substrate", Nano Letters, 2006, pp. A-G.
Sherry, et al., "Localized Surface Plasmon Resonance Spectroscopy of Single Silver Triangular Nanoprisms", Nano Letters, 2006, vol. 6, No. 9, pp. 2060-2065.
Shuford, et al., "Optical Properties of Gold Pyramidal Shells", J. Phys. Chem. C., 2008, pp. A-E.
Srivastava, et al., "Nanorice and Nanospears from Polymer Nanospheres", Advanced Materials, 2006, 18, pp. 2471-2475.
Su, et al., "Raman Enhancement Factor of a Single Tunable Nanoplasmonic Resonator", J. Phys. Chem. B, 2006, vol. 110, No. 9, pp. 3964-3968.
Su, et al., "Tunable and augmented Plasmon resonances of Au/SiO$_2$/Au nanodisks", Applied Physics Letters, 2006, 88, pp. 063118-1-063118-3.
Sun, et al., "Shape-Controlled Synthesis of Gold and Silver Nanoparticles", Science, 2002, vol. 298, pp. 2176-2179.
Sun, et al., "Synthesis and Optical Properties of Nanorattles and Multiple-Walled Nanoshells/Nanotubes Made of Metal Alloys", J. Am. Chem. Soc., 2004, vol. 126, No. 30, pp. 9399-9406.
Tao, et al., "Langmuir-Blodgett Silver Nanowire Monolayers for Molecular Sensing Using Suface-Enhanced Raman Spectroscopy", Nano Letters, 2003, vol. 3, No. 9, pp. 1229-1233.
Tao, et al., "Tunable plasmonic lattices of silver nanocrystals", Nature, 2007, vol. 2, pp. 435-440.
Tao, et al., "Self-Organized Silver Nanoparticles for Three-Dimensional Plasmonic Crystals", Nano Letters, 2008, vol. 8, No. 11, pp. 4033-4038.
Wang, et al., "Near-infrared surface-enhanced Raman scattering of a kind of self-assemblies film based on coordination bond", Materials Science & Engineering C, 1999, 10, pp. 3-6.
Wang, et al., "Monodispersed Core-Shell Fe$_3$O$_4$@Au Nanoparticles", J. Phys. Chem. B, 2005, vol. 109, No. 46, pp. 21593-21601.
Wang, et al.,"Nanorice: A hybrid Plasmonic Nanostructure", Nano Letters, 2006, 6(4), pp. 827-832.
Wang, et al., "Mesoscopic Au "Meatball" Particles", Advanced Materials, 2008, 20, pp. 820-825.
Wiley, et al., "Synthesis and Optical Properties of Silver Nanobars and Nanorice", Nano Letter, 2007, 7(4), pp. 1032-1036.
Wu, et al., "Seed-Mediated Synthesis of Branched Gold Nanocrystals Derived from the Side Growth of Pentagonal Bipyramids and the Formation of Gold Nanostars", Chem. Mater., 2009, 21, pp. 110-114.
Xiang, et al., "Gold Nanorod-Seeded Growth of Silver Nanostructures: From Homogeneous Coating to Anisotropic Coating", Langmuir, 2008, pp. A-F.
Xie, et al., "The Synthesis of SERS-Active Gold Nanoflower Tags for in Vivo Applications", ACS Nano, 2008, pp. A-H.
Xu, et al., "Precious Metal Core-Shell Spindles", J. Phys. Chem. C, 2007, pp. A-H.
Ye, et al., "Fabrication, Characterization, and Optical Properties of Gold Nanobowl Submonolayer Structures", Langmuir, 2009, 25(3), 1822-1827.
Yoo, et al., "Core-Shell Triangular Bifrustums", Nano Letters, 2009, vol. 9, No. 8, pp. 3038-3041.
Zeng, et al., "Controlling the Shapes of Silver Nanocrystals with Different Capping Agents", J. Am. Chem. Soc., 2010, vol. 132, No. 25, pp. 8552-8553.
Zhang, et al., "Monodisperse Icosahedral Ag, Au, and Pd Nanoparticles: Size Control Strategy and Superlattice Formation", ACS Nano, 2008, pp. A-J.

(56) References Cited

OTHER PUBLICATIONS

Zhang, et al., "Seed-Mediated Synthesis of Ag Nanocubes with Controllable Edge Lengths in the Range of 30-200 nm and Comparison of Their Optical Properties", J. Am. Chem. Soc., 2010, vol. 132, No. 32, pp. 11372-11378.

Zhang, et al., "Concave Cubic Gold Nanocrystals with High-Index Facets", J. Am. Chem. Soc., 2010, vol. 132, No. 40, pp. 14012-14014.

Zhao, et al., "Polarized Surface Enhanced Raman and Absorbance Spectra of Aligned Silver Nanorod Arrays", J. Phys. Chem. B, 2006, vol. 110, No. 7, pp. 3153-3157.

Dai, et al., "A "Nanonecklace" Synthesized from Monofunctionalized Gold Nanoparticles", J. Am. Chem. Soc., 2005, vol. 127, No. 22, pp. 8008-8009.

Dietrich-Buchecker, et al., "Templated Synthesis of Interlocked Macrocyclic Ligands: The Catenands", J. Am. Chem. Soc., 1984, vol. 106, No. 10, pp. 3043-3045.

Kaim, et al., "Unconventional Mixed-Valent Complexes of Ruthenium and Osmium", Angewandte Chemie International Edition, 2007, vol. 46, Issue 11, pp. 1778-1796.

Sanles-Sobrido, et al., "Design of SERS-Encoded, Submicron, Hollow Particles Through Confined Growth of Encapsulated Metal Nanoparticles", J. Am. Chem. Soc., 2009, 131(7), pp. 2699-2705.

Sauvage, "Interlacing Molecular Threads on Transition Metals: Catenands, Catenates, and Knots", Acc. Chem. Res., 1990, vol. 23, No. 10, pp. 319-327.

Schwartzberg, et al., "Gold Nanotubes Synthesized via Magnetic Alignment of Cobalt Nanoparticles as Templates", J. Phys, Chem. C, 2007, 111 (44), pp. 16080-16082.

Sieb, et al., "Hollow Metal Nanorods with Tunable Dimensions, Porosity, and Photonic Properties", ACS Nano, 2009, vol. 3, No. 6, pp. 1365-1372.

Tam, et al., "Mesoscopic Nanoshells: Geometry-dependent Plasmon resonance beyond the quasistatic limit", J. Chem. Phys., 2007, 127, pp. 204703-1-204703-6.

Chen, et al., "Catalytically active gold on ordered titania supports", Chem. Soc. Rev., 2008, 37, pp. 1860-1870.

Coquet, et al., "Theory and simulation in heterogeneous gold catalysis", Chem. Soc. Rev., 2008, 37, pp. 2046-2076.

Corma, et al., "Supported gold nanoparticles as catalysts for organic reactions", Chem. Soc. Rev., 2008, 37, pp. 2096-2126.

Fierro-Gonzalez, et al., "Catalysis by gold dispersed on supports: the importance of cationic gold", Chem. Soc. Rev., 008, 37, pp. 2127-2134.

Gimeno, et al., "Chalcogenide centred gold complexes", Chem. Soc. Rev., 2008, 37, pp. 1952-1966.

Grzelczak, et al., "Shape control in gold nanoparticles synthesis", Chem. Soc. Rev., 2008, 37, pp. 1783-1791.

Hakkinen, et al.,"Atomic and electronic structure of gold clusters: understanding flakes, cages and superatoms from simple concepts", Chem. Soc. Rev., 2008, 37, pp. 1847-1859.

Hashmi, et al., "Gold catalysis in total synthesis", Chem. Soc. Rev., 2008, 37, pp. 1766-1775.

Hutchings, et al., "Gold-an introductory perspective", Chem. Soc. Rev., 2008, 37, pp. 1759-1765.

Jansen, "The chemistry of gold as an anion", Chem. Soc. Rev., 2008, 37, pp. 1826-1835.

Katz, et al., "The use of aurophilic and other metal-metal interactions as crystal engineering designs elements to increase structural dimensionality", Chem. Soc. Rev., 2008, 37, pp. 1884-1895.

Laaksonen, et al., "Quantised charging of monolayer-protected nanoparticles", Chem. Soc. Rev., 2008, 37, pp. 1836-1846.

Marion, et al., "N-Heterocyclic carbenes in gold catalysis", Chem. Soc. Rev., 2008, 37, pp. 1776-1782.

Myroshnychenko, et al., "Modelling the optical response of gold nanoparticles", Chem. Soc. Rev., 2008, 37, pp. 1792-1805.

Ofir, et al., "Polymer and biopolymer mediated self-assembly of gold nanoparticles", Chem. Soc. Rev., 2008, 37, pp. 1814-1825.

Pina, et al., "Selective oxidation using gold", Chem. Soc. Rev., 2008, 37, pp. 2077-2095.

Prasad, et al., "Gold nanoparticle superlattices", Chem. Soc. Rev., 2008, 37, pp. 1871-1883.

Puddephatt, et al., "Macrocycles, catenanes, oligomers and polymers in gold chemistry", Chem. Soc. Rev., 2008, 37, pp. 2012-2027.

Pyykko, "Theoretical chemistry of gold. III", Chem. Soc. Rev., 2008, 37, pp. 1967-1997.

Raubenheimer, et al., "Carbene complexes of gold: preparation, medical application and bonding", Chem. Soc. Rev., 2008, 37, pp. 1998-2011.

Schmid, "The relevance of shape and size of $Au_{55}$ clusters", Chem. Soc. Rev., 2008, 37, pp. 1909-1930.

Schmidbaur, et al., "A briefing on aurophilicity", Chem. Soc. Rev., 2008, 37, pp. 1931-1951.

Sperling, et al., "Biological applications of gold nanoparticles", Chem. Soc. Rev., 2008, 37, pp. 1896-1908.

Wilson, "The use of gold nanoparticles in diagnostics and detection", Chem. Soc. Rev., 2008, 37, pp. 2028-2045.

Wing-Wah, et al., "Highlights on the recent advances in gold chemistry-a photophysical perspective", Chem. Soc. Rev., 2008, 37, pp. 1806-1813.

\* cited by examiner

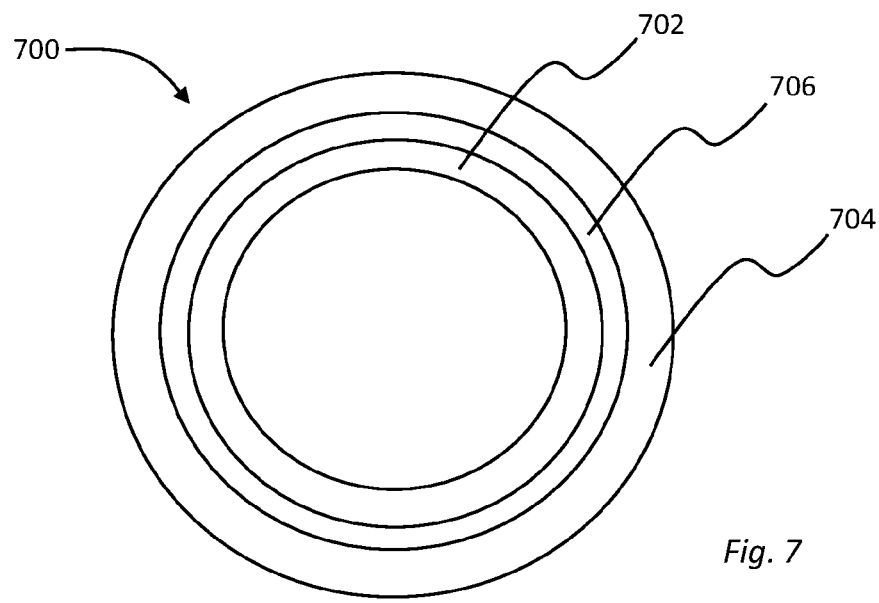
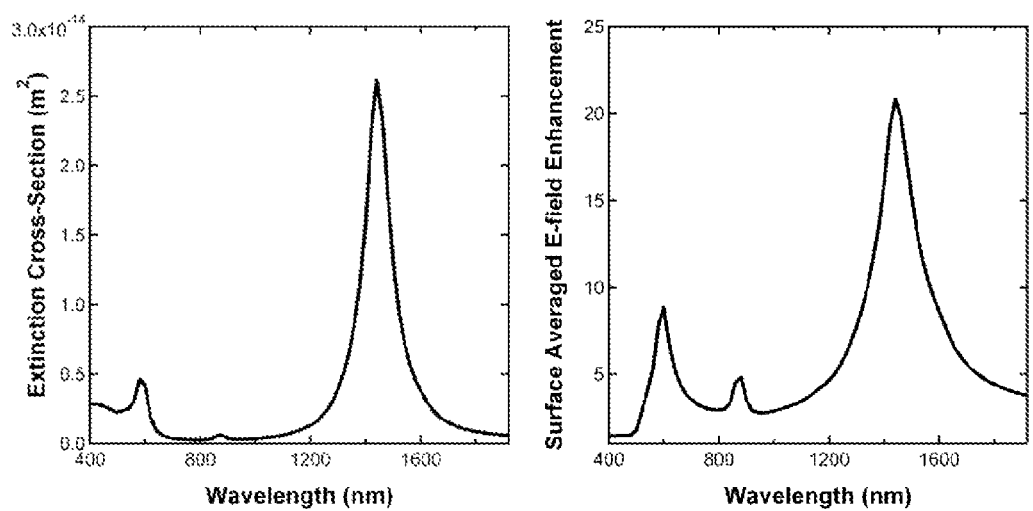
Fig. 7
Fig. 8

PARTICLES COMPRISING HOLLOW SURFACE-ENHANCED SPECTROSCOPY (SES)-ACTIVE CORE FOR LONG WAVELENGTH SERS

RELATED APPLICATIONS

This application is a 35 U.S.C. §371 national phase application of PCT/US10/35300 (WO 2010/135354), filed on May 18, 2010, entitled "Particles and Methods for Long Wavelength SERS", which application claims the benefit of U.S. Provisional Application Ser. No. 61/179,281, filed May 18, 2009, and U.S. Provisional Application Ser. No. 61/181,598, filed May 27, 2009, which are incorporated herein by reference in its entirety.

TECHNICAL FIELD

The present application is directed toward Surface Enhanced Raman Spectroscopy methods and particles and more particularly toward particles which enhance Raman scattering at long wavelengths.

BACKGROUND

When light is directed onto a molecule, the vast majority of the incident photons are elastically scattered without a change in frequency. This is termed Rayleigh scattering. However, the energy of some of the incident photons (approximately 1 in every $10^7$ incident photons) is coupled into distinct vibrational modes of the molecule's bonds. Such coupling causes some of the incident light to be inelastically scattered by the molecule with a range of frequencies that differ from the range of the incident light. This is termed the Raman effect. By plotting the frequency of such inelastically scattered light against its intensity, the unique Raman spectrum of the molecule or material under observation is obtained. Analysis of the Raman spectrum of an unknown sample can yield information about the sample's molecular composition.

The intensity of Raman scattered radiation can be significantly increased by bringing the Raman-active molecule(s) or materials in very close proximity (for example ≤20 Å) to certain types of nanostructured metal surfaces. For example, molecules adsorbed to roughened gold, silver or copper or other free electron metal surfaces can experience million-fold increases in Raman intensity. This effect, called surface enhanced Raman scattering and alternately surface enhanced Raman spectroscopy (in both cases referred to as SERS) can be observed with metal colloidal particles, metal films on dielectric substrates, with ordered or disordered metal particle arrays, and on a variety of other nanoscopic, mesoscopic, microscopic, or macroscopic surfaces.

The mechanism by which SERS or similar surface enhanced spectroscopic (SES) phenomena occur is understood, and is thought to result from a combination of electromagnetic (e.g. local field) and chemical (e.g. charge transfer) effects. Representative SES techniques include, but are not limited to surface enhanced Raman spectroscopy (SERS) and surface enhanced resonance Raman spectroscopy (SERRS). In SERS or SERRS, the metal or other enhancing surface will couple electromagnetically to incident electromagnetic radiation and create a locally amplified electromagnetic field that leads to $10^2$- to $10^9$-fold or greater increases in the Raman scattering of a SERS active molecule situated on or near the enhancing surface.

As noted above, Raman scattering occurs when a molecule is illuminated with incident light. Typically, the incident light source is a monochromatic laser. The correct selection of the incident laser wavelength can be an important consideration for Raman spectroscopy. For instance, many samples, especially those of an organic or biological nature will be (or contain) fluorescent species. Exciting these samples with a laser in the green (532 nm) may promote fluorescence, which will swamp any underlying Raman spectrum to such an extent that it is no longer detectable.

Accordingly, Raman spectroscopy techniques such as SERS and SERRS often feature the use of a laser in the red, for example, 633 nm or near infrared (NIR), for example, 785 nm or 1064 nm portions of the spectrum. Since these sources have somewhat lower photon energy that green or shorter wavelength sources, a red or NIR laser may not promote the electronic transitions which will resulting in fluorescence, resulting in Raman scattering which is easier to detect.

Unfortunately, as the incident wavelength is increased, from green to red to NIR, the efficiency of Raman scattering decreases, since it varies as $(1/\text{wavelength})^4$. Therefore, longer integration times and/or higher power lasers are necessary to acquire a suitable signal as the incident wavelength increases. Typically, lasers emitting light having a wavelength of no longer than about 1064 nm are used for Raman spectroscopy. Longer wavelengths result in such diminished scattering efficiency that the use of longer wavelength sources is impractical.

Certain safety concerns are present when using shorter wavelength lasers. In particular, lasers emitting at 1064 nm, 785 nm and shorter wavelengths are potentially hazardous if directed into a human eye. The maximum eye-safe exposure to laser light increases dramatically at 1400 nm and longer wavelengths as shown in the graphs 100 and 102 of FIG. 1, taken from the American National Standards Institute (ANSI) Standard Z136.1-2007. Accordingly, Raman microscopes or Raman spectrometers which use lasers emitting at 1064 nm or shorter wavelengths must be either stationary devices that cannot inadvertently illuminate a technician's eye, or these devices must include complex safety mechanisms to avoid the possibility of accidental damage to a technician's eye. Safety concerns thus limit the feasibility of hand held or other laser sources which may be implemented in a variety of uncontrolled, non-laboratory situations. Longer wavelength radiation can be relatively eye-safe; however as described above, longer wavelength light sources result in inefficient scattering using known enhancement strategies.

Generally, the suitability of a particle-based enhancing surface for use at longer wavelengths can be improved by making the particle larger, because larger particles typically exhibit plasmon bands shifted further into the NIR relative to smaller particles. Many SES active taggants are designed for use or dispersion in fluids, and thus are best implemented with particles or tags that are sized and have a suitable density to remain suspended in the selected liquid without settling. Therefore, the design of particles that may be interrogated at longer, eye-safe wavelengths and are also suspendable in a liquid is particularly problematic.

The present invention is directed toward overcoming one or more of the problems discussed above.

SUMMARY

One embodiment includes a particle comprising a surface enhanced spectroscopy (SES)-active core and a SES-active reporter molecule associated with the SES-active core wherein said particle has a measurable SES spectrum when excited by incident light having a wavelength of at least 1400 nm. The particle of this embodiment may include an SES-active core which supports plasmon resonance at a wavelength of at least 1400 nm. The particle may comprise an anisotropic core. For example, the particle may include but is not limited to implementations with hollow cores, hollow rod cores, hollow Cu rod cores, interlocking nanoring cores, a hollow core of one or more layers, or a core comprising an aggregate of nanoparticles.

The particle may be suspendable in a liquid solvent. Particle suspension may be improved or achieved in any suitable manor, for example, an organic coating may be applied, surrounding other particle structures.

The particle may include an SES-active reporter molecule which is resonant at one or more wavelengths greater than or equal to 1400 nm. The reporter molecule may be, but is not limited to, a transition metal complex, a transition octahedral metal d8 complex, an aromatic compound or an intervalence transfer complex.

An alternative embodiment includes a method of manufacturing a particle as described above which particle produces a measurable SES spectrum when excited by incident light having a wavelength of at least 1400 nm.

An alternative embodiment includes a method of tagging a material comprising providing a particle as described above which has a measurable SES spectrum when excited by incident light having a wavelength of at least 1400 nm and associating the particle with a material of interest.

An alternative embodiment includes a detection system comprising a particle as described above and a detector having an illumination source providing illumination at a wavelength of at least 1400 nm.

BRIEF DESCRIPTION OF THE DRAWINGS

FIG. 7 is a schematic representation of a particle having a core including multiple concentric layers.

FIG. 8 is graphic representation of the results of a simulation predicting the plasmon resonance of a particle having a core of aggregated nanoparticles.

DESCRIPTION

Figure 1:
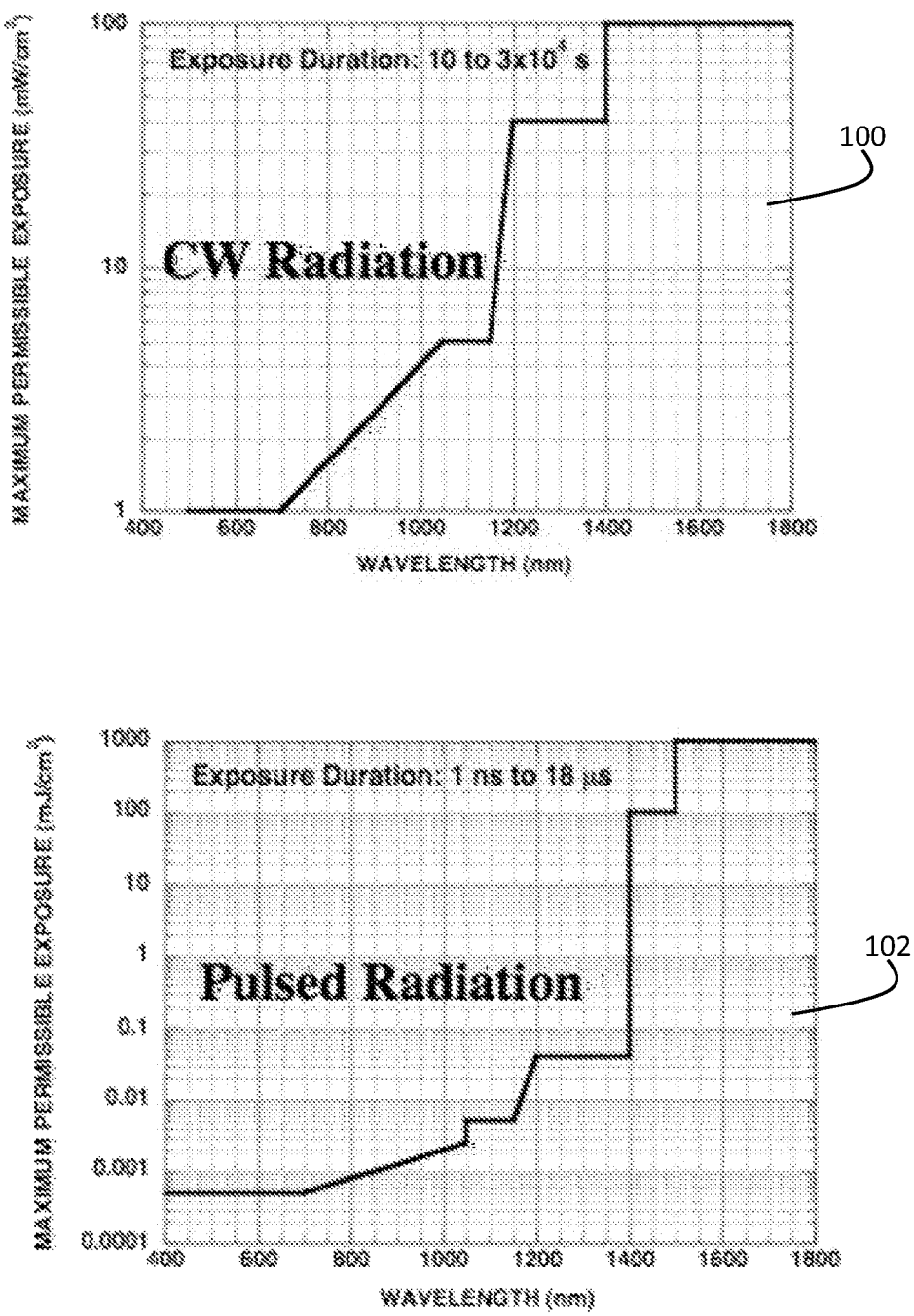
FIG. 1 is a graphic representation of the maximum permissible exposure to monochromatic laser radiation as a function of wavelength.

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

In general, taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, barcoding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection or identification.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

The addition of taggants to liquids, and in particular liquid hydrocarbons such as fuel, diesel oil, gasoline, kerosene, ethanol, biodiesel, methanol, crude oil, fuel additives, etc. is recognized to be useful for the reasons described above. Similarly, the addition of a taggant allows protection against counterfeiting, or use of the hydrocarbon in an improper setting (i.e. brand diversion). Likewise, the ability to measure the concentration of a taggant in a hydrocarbon allows a determination of purity: if the concentration is lower than added, it suggests that the sample has been tampered with (for example by addition of a less valuable hydrocarbon). Often, this tampering can be at the level of a 1-5%, so highly accurate and precise measurements of taggants are required. Measuring taggant concentration can also be invaluable for process monitoring, where crude oil (for example) is often mixed with mud, steam, water, and other impurities, and where knowledge of the actual oil concentration impacts how selected processes are carried out. In another example, when fuel products with different owners share the same infrastructure (e.g. a pipeline), a tagged fuel allows operators to know which fuel is at which location at which time.

Likewise, the addition of a taggant also provides insurance against legal liability. For example, the absence of taggant in a spilled sample of oil or gasoline allows fuel owners who have added taggant to their oil or gasoline to be exempt from liability. In many cases, the use of known taggants results in insufficient precision, detection accuracy or other problems.

Taggants can be also used for a variety of other liquids, including but not limited to liquid medications, liquid pharmaceuticals, and liquid medicines. Taggants can also be used to assist in process monitoring for other liquids. For instance, the growth of e. coli bacteria could be followed using a taggant. Likewise, taggants could be used to monitor consumption of material, e.g. fuel in tank. This could be true for a liquid or a solid fuel.

Taggants can also be useful for tracking of solid materials, e.g. bulk chemicals and materials, powders, mixtures, polymers, etc. For example, taggants could be used to materials thought be used in the development of explosives.

Taggants can also be used to track plants and other things, e.g. animals

Taggants can also be used track molecules, biomolecules, macromolecules, biopolymers, cells, and macromoleculer assemblies, in other words for any number of life science applications, including but not limited to in vitro and in vivo diagnostics. In these applications, taggants are typically referred to as "optical detection labels" or "optical quantition labels". For the same reasons described above, taggants/labels that can be used at long excitation wavelengths would be useful in tracking of other liquids, solids, living objects, and for life science applications.

Many known methods of detecting taggants utilize one of several spectroscopic techniques, for example a surface-enhanced spectroscopy (SES) techniques such as SERS or SERRS. An extraordinarily large number of SERS-active materials exist. Broadly speaking, suitable materials fall in two categories: nano-/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

Known prior art tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate.

Several of the disclosed materials and methods feature the use of a surface-enhanced spectroscopy (SES) active taggant. Representative SES techniques include but are not limited to SERS, SERRS and others. Surface enhancement in various other spectroscopy methods or systems has been observed. The most widely studied have been surface-enhanced Raman scattering and surface-enhanced fluorescence (SEF). However, a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure and claims SES includes the above listed and any related or similar spectroscopic technique.

Many of the examples herein are described with respect to SERS. It must be noted however that the methods, compositions and particles disclosed herein are equally applicable to SERRS, SEHRS, SEF, SEHRRS, SHG, SEIRA, SPASERS, or other surface enhanced or plasmon enhanced SES technique.

As noted above, one type of known SERS-active nanoparticle is a SERS nanotag, as described in U.S. Pat. No. 6,514,767, No. 6,861,263, No. 7,443,489 and elsewhere. All matters disclosed in U.S. Pat. No. 6,514,767, No. 6,861,263 and No. 7,443,489 are incorporated herein in their entirety for all matters disclosed therein. In a conventional SERS nanotag composition, a reporter molecule is adsorbed to a SERS-active surface, and both the SERS-active surface and the reporter are encapsulated, typically with silica. One advantage of a silica coating is that it prevents the adsorbed molecule from diffusing away, and also prevents other molecules from adsorbing to the surface. This imparts a level of robustness and environmental insensitivity to the SERS nanotag particles that is, for many applications, a desirable feature. A typical SERS nanotag may be excited by incident radiation in the red or NIR portions of the electromagnetic spectrum, for example incident light at 633 nm. As described above, Raman scattering efficiency decreases as the wavelength of the incident light increases.

Figure 2:
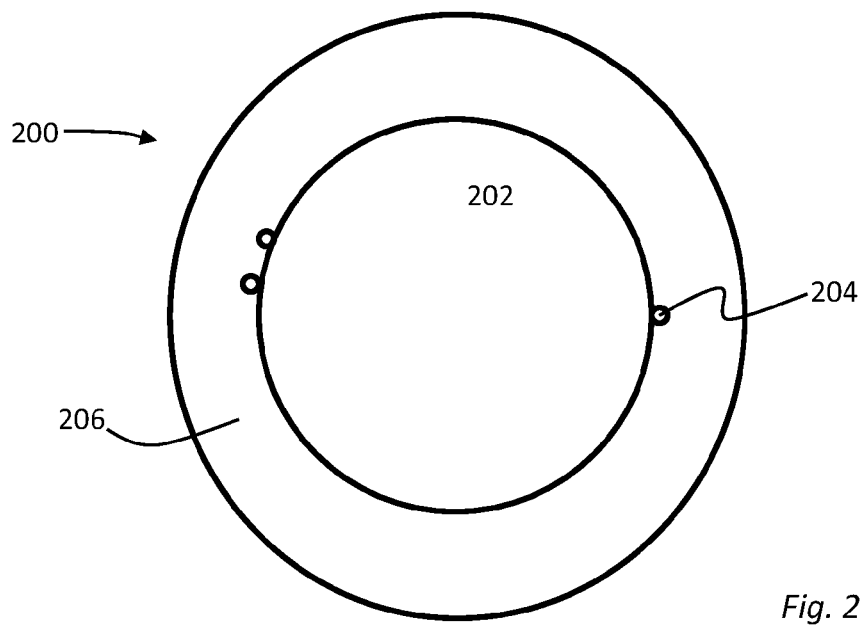
FIG. 2 is a schematic representation of a prior art SERS nanotag.

A typical SERS nanotag may be fabricated as the three-component nanoscale particle 200 illustrated in FIG. 2. The first component is a generally spherical SERS-enhancing metal core 202. The core may be, but is not limited to, a solid gold (Au) sphere of about 90 nm diameter, but other metals, shapes and sizes are possible. The role of the core 202 is to couple electromagnetically to incident laser radiation and create a locally amplified electromagnetic field that leads to $10^2$- to $10^9$-fold increases in Raman scattering intensity. The second component is a SES active "reporter," 204, a molecule or other spectroscopically active material in close proximity (and ideally adsorbed) to the core surface. The output in a SERS experiment is the fingerprint-like vibrational spectrum of the reporter, the intensity of which is proportional to polarizability. The third component of a conventional short-wavelength tag is an encapsulant 206. Typically the encapsulant is $SiO_2$, a polymer, or other suitable material. The primary roles of the encapsulant 206 are to prevent the reporter 204 from diffusing away the core surface, and to prevent other species (that could generate confounding fingerprints) from reaching the surface.

As described in U.S. Pat. No. 6,514,767, No. 6,861,263, No. 7,443,489, known SERS nanotags are excited using laser light in the red or near infrared portions of the spectrum. For example, Raman lasers emitting at 633 nm, 785 nm or 1064 nm are commercially available and suitable for use with conventional SERS active particles. As illustrated in FIG. 1, these wavelengths are not eye-safe. As defined herein, any excitation wavelength of less than 1400 nm is not "eye-safe." Wavelengths of greater than 1400 nm are defined as eye-safe. In particular, commercially available lasers emitting at 1432 nm and about 1550 nm are defined as eye-safe. SERS nanotags as described in the U.S. Pat. No. 6,514,767, No. 6,861,263, No. 7,443,489 are not suitable for use with an eye-safe laser source of reasonable power because Raman scattering efficiency using the core configurations and reporter types disclosed therein are dramatically reduced at longer, eye-safe, wavelengths. As described above, many taggant embodiments require tags or particles that may be suspended for a selected period of time, or indefinitely, in a liquid matrix. Eye-safe excitation favors larger particles, while suitability for long-term suspended dispersal in a liquid matrix favors smaller particles. Accordingly, the design of a suspendable, SERS tag that can be used at eye-safe wavelengths is particularly problematic.

The challenge of preparing SERS taggants useful at eye-safe excitation wavelengths, for example about 1432 nm and about 1550 nm cannot be underestimated. There is currently no literature describing SERS at such wavelengths. The bulk of any type of SES enhancement comes from electromagnetic resonances due to the localized surface plasmon of the metal surface. For the most common spherical metal nanoparticles, Ag and Au, the surface plasmon of individual particles is located near 400 and 530 nm, respectively. By making aggregates of the particles, or by making non-spherical particles, the plasmon may be shifted further into the red and infrared. Spherical Au does not support significant plasmon resonances at 1550 nm, even when heavily aggregated. Therefore, moving to 1550 nm excitation will typically require novel core configurations; which is made more challenging if the particle is required to also remain suspended in a solvent. One approach to these goals features anisotropic particle cores, and possibly, cores comprising one or more hollow layer structures as described in detail below.

An alternative embodiment of particle that may be efficiently excited at eye-safe wavelengths incorporates novel reporter molecules either with a conventional spherical core, or with an anisotropic core. It is important to note that the goal of a SES active particle or taggant that may be excited at eyesafe wavelengths may be achieved with a novel core configuration, a novel reporter or a combination of these techniques.

Long Wavelength Particles with Anisotropic Cores

A. Hollow Nanotubes

The ability of a particle to remain suspended in a liquid may be enhanced by reducing particle mass. Hollow particles may be prepared which feature cores of reduced mass while retaining most of the optical properties of larger cores. For example, a hollow metal rod is expected to have a plasmon resonance in the Near-IR. Au nanotubes have been synthesized by galvanic replacement starting with Ag rods. *Hollow Metal Nanorods with Tunable Dimensions, Porosity, and Photonic Properties*, Nathanael R. Sieb, Nien-chen Wu, Elham Majidi, Richa Kukreja, Neil R. Branda, and Byron D. Gates, ACS Nano, Article ASAP•DOI: 10.1021/nn900099t•Publication Date (Web): 13 May 2009. This particular example shows a shift of the Au plasmon to 750 nm. Constructing nanotubes with Cu should shift the Plasmon band further toward longer wavelengths. Gold Nanotubes have also been prepared by fusing of Au nanospheres. *Alignment of Cobalt Nanoparticles as Templates*, Adam M. Schwartzberg, Tammy Y. Olson, Chad E. Talley, and Jin Z. Zhang J. Phys. Chem. C, 2007, 111 (44), 16080-16082•DOI: 10.1021/jp076034b•Publication Date (Web): 5 Oct. 2007.

Alternatively, tubes could be made directly by deposition of a metal, for example AU, Ag or Cu on the interior of a template such as an anodically grown alumina membrane or an array of glass tubes. The membrane would then be dissolved, resulting in a freed metal nanotube.

Figure 3:
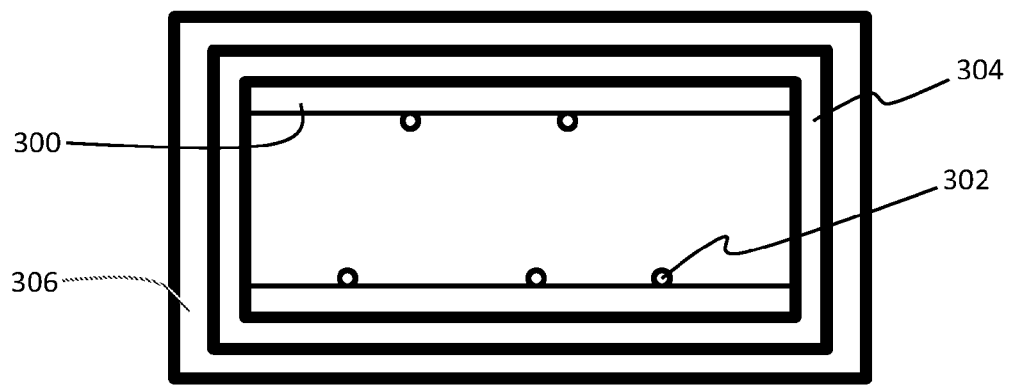
FIG. 3 is a schematic representation of a tag having a hollow nanotube core.

As shown in FIG. 3, the interior of a nanotube 300 can be coated with a SERS reporter molecule 302. A protective layer 304 such as silica or another metal oxide can be grown or deposited on the exterior of the structure to provide isolation from the environment. Finally, an organic molecule or organic coating 306 can be attached to the protective layer 304 to provide improved solubility in non-polar solvents.

B. Interlocking Nanorings

Figure 4:
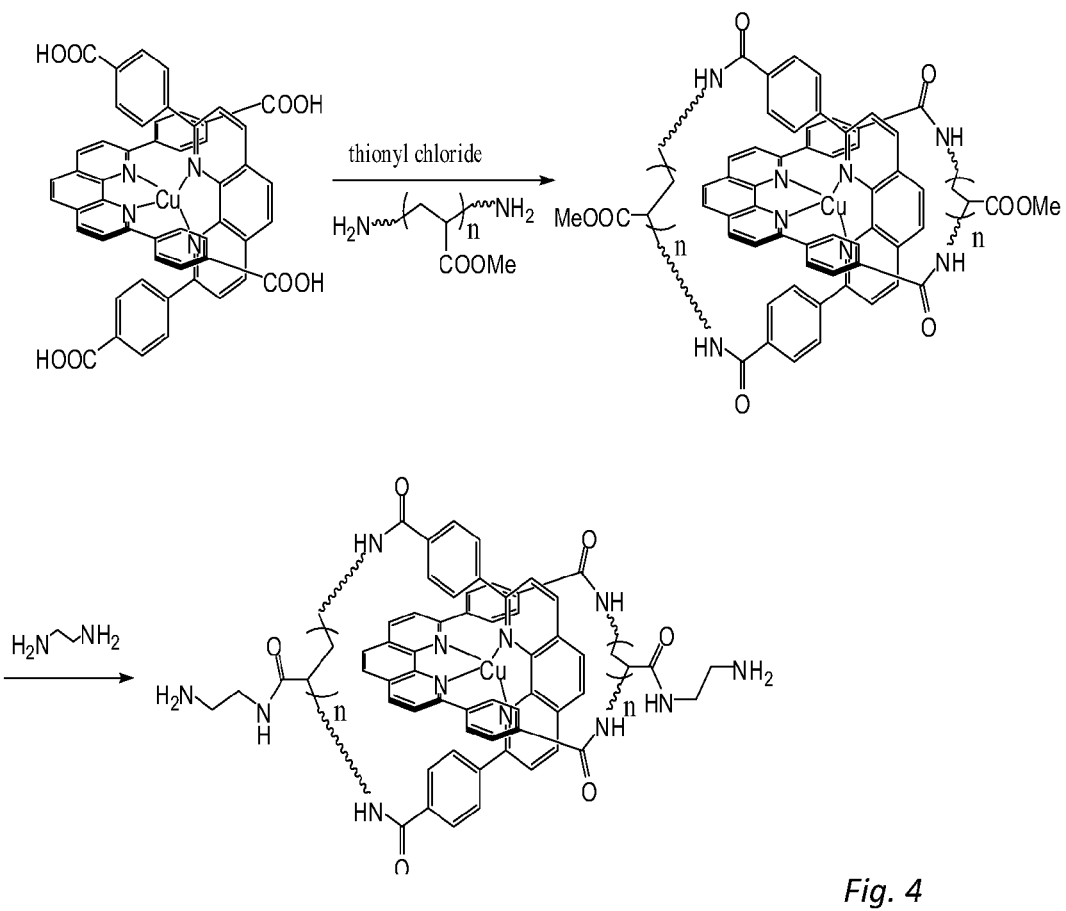
FIG. 4 is diagram representing a method of fabricating linked nanorings.

An alternative anisotropic core configuration which may be suitable for eye-safe SERS particles features a core of interlocking nanorings. The preparation of interlocked gold rings can be accomplished by the use of an organic catenane template. In order to prepare nanosized rings it is necessary to work with polymeric catenanes. A polymeric catenane may be prepared as shown in FIG. 4 by derivatizing a tetracoordinate metal-ligand complex with an amino polyacrylate polymer, followed by the amidation of the ester groups with excess ethylenediamine, as described in C. O. Dietrich-Buchecker, J.-P. Sauvage, J. P. Kintzinger, *Tetrahedron Lett.* 1983, 24, 5095; C. O. Dietrich-Buchecker, J.-P. Sauvage, J. M. Kern, *J. Am. Chem. Soc.* 1984, 106, 3043 and J.-P. Sauvage, *Acc. Chem. Res.* 1990, 23, 319. The size of the rings can be governed by the molecular weight of the polymer. The polyaminated catenane can then be used as the template for the formation of the gold rings. Small monofunctionalized gold nanoparticles can be covalently attached to the amino groups of the polymer, forming a string of nanoparticles; D. Qiu, J. G. Worden, J. Trullinger, Q Huo, *J. Am. Chem. Soc.* 2005, 127, 8008. Growth of gold around the nanoparticle string would yield interlocked gold rings. Decomplexation from the Cu atom may be done before or after the gold growth.

Figure 5:
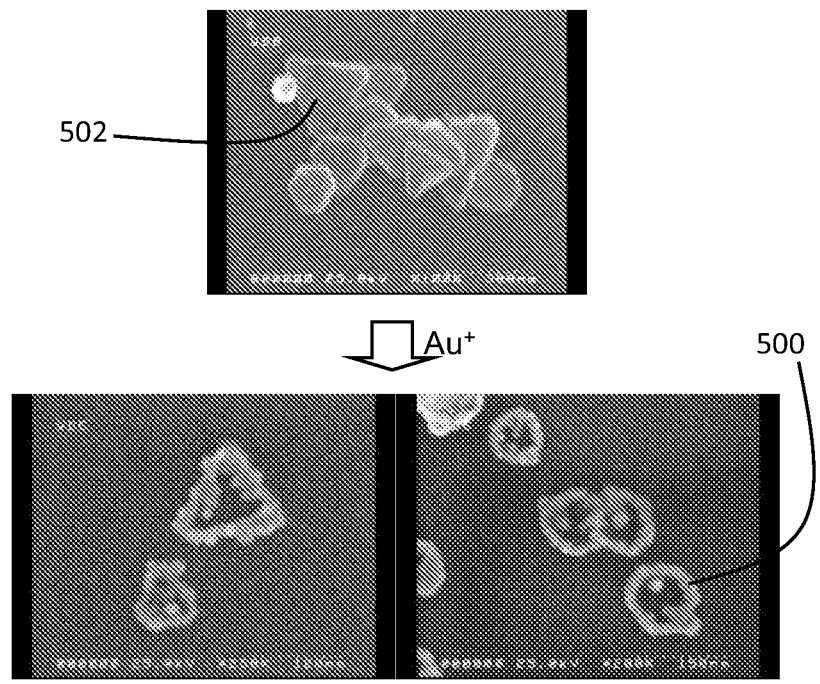
FIG. 5 is an electron microscope image of nanoprisms and nanorings.

Alternatively, galvanic replacement can be used to create hollow Au nanoparticles from Ag nanoparticle templates. In this embodiment, as shown in FIG. 5, Au rings 500 can be created from Ag nanoprisms 502. Ag nanoprisms are flat Ag nanoparticles that vary in shape from triangles to hexagons to disks. When Au ions are introduced to the Ag nanoprism solution, the Ag is replaced with Au, creating hollow rings of Au that are shaped like the starting template. *ACS Nano*, 2009, 3 (6), pp 1365-1372

C. Hollow Spheres and Cubes

Figure 6:
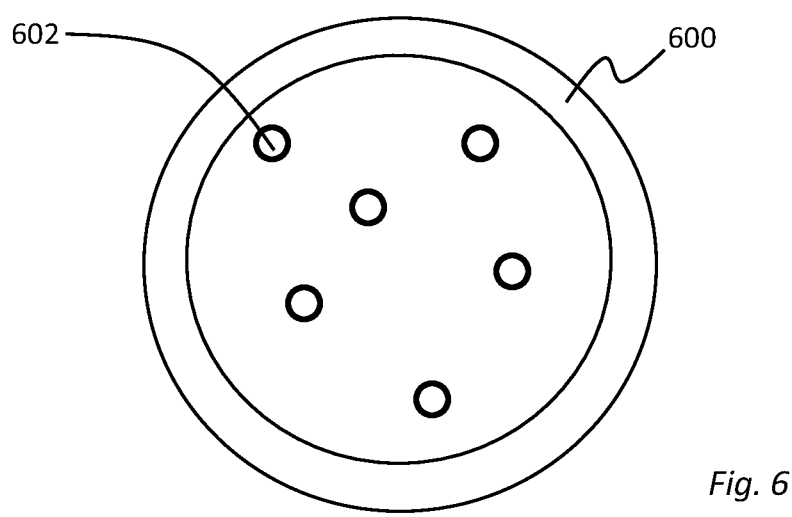
FIG. 6 is a schematic representation of a hollow shell particle with reporter molecules located within the shell.

Hollow spherical particles may be made by following a growth template-shell approach. The growth template may be non-metallic (polystyrene, silica, etc.) in which case the shell is added to the exterior by a seeded growth mechanism. First small seed colloids (often Au) are attached to the exterior of a silica or polymer bead. Additional Au is then grown resulting in a continuous shell. Because the shell can be prepared with some pores, the growth template particle is then readily removed by dissolving the growth template with the appropriate chemical. As an example, Tam et al. have prepared relatively large hollow particles with plasmon resonances at 1900 nm. *Mesoscopic nanoshells: Geometry-dependent plasmon resonances beyond the quasistatic limit*, Felicia Tam, Allen L. Chen, Janardan Kundu and Hui Wang, Naomi J. Halas J. Chem. Phys. 127, 204703, 2007. Alternatively, if a Ag particle is used as the growth template, galvanic displacement of the Ag by Au has been used to prepared both hollow spheres and hollow cubes. As shown in FIG. 6, once a hollow shell 600 is prepared, reporter molecules 602 may be inserted into the interior of the particle, followed by a reaction to seal the interior.

D. Hollow Oblate Spheroids

A similar growth template-shell approach as described above with respect to spheres can be taken with non-spherical cores. One example of this type of particle has a hematite core, a 9.8 nm Au shell and extinction maximum at 1250 nm. *Nanorice: A Hybrid Plasmonic Nanostructure*, Hui Wang, Daniel W. Brandl, Fei Le, Peter Nordlander, and Naomi J. Halas Nano Lett., 2006, 6 (4), 827-832•DOI: 10.1021/nl060209w•Publication Date (Web): 11 Mar. 2006.

E. Particles with Hollow, Multi-Layered Cores

Several theoretical papers report that multilayer particles have narrow plasmon resonances with large electromagnetic field enhancements. A SERS active nanoparticle core having finely tuned plasmon characteristics may thus be comprised of multiple slayers. The SERS enhancing core may include both the metal being used for plasmonics, as well as layers (such as dielectrics) that may be used as spacers to create well-defined gaps between metal layers. For example, as shown in FIG. 7, a hollow SERS enhancing core 700 comprised of multiple metal layers 702, 704 should provide additional SERS enhancement and the ability to tune the plasmon resonance to the infrared. The electromagnetic field experienced between the metallic layers should be similar to that found in the junctions between two adjacent particles, as the optical response of both systems is driven by the interaction of two distinct plasmons. By controlling the thickness and composition of each layer, precise tuning of the optical response should be possible.

The metal inner layer 702 of a hollow SERS active nanoparticle core 700 comprised of multiple layers could consist of any of the hollow core structures described above. A reporter-doped dielectric layer 706, such as silica or a polymer, could then be grown over this inner layer 702 of the hollow multi-layered core 700. For instance, a reporter molecule such as an aromatic thiol can be bound to the innert layer 702, and then a silica dielectric layer 706 can be grown over the inner layer 702 through the Stober process. The dielectric layer 706 would then be modified for the growth of the outer metal layer 704 of the hollow multi-layered core 700. For instance, in the case of a silica dielectric layer 706, the same process as described above for a single layer particle can be used. Alternatively, if a positively charged polymer is used as the dielectric layer 706, Au seed particles can be bound to the polymer electrostatically as described by Sanles-Sobrido, et al., JACS. 2009, 131, 2699-2705, which would then be used for subsequent seed-mediated growth of the outer metallic layer 704.

It would be advantageous to have metals deposited over other core materials with thickness tolerances of 2-5 nm in order to tailor sufficiently well defined plasmon responses. Layer thickness has a greater impact on optical behavior for particles having multi-layered metal cores than for solid metals. This is demonstrated by the extinction profiles of Au shells over hematite cores, which are observed to be redshifted approximately 200 nm as Au shells increase from 9.3 to 27.5 nm. Using existing methods, the thinnest gold shells will be partially defined by the size and density of Au nanoparticle 'primer' coatings, and are likely to be almost 10 nm. However, thicker shells may be etched to define a relatively thin final construct. An etchant such as KCN may be used in conjunction with real-time monitoring of the extinction profile, and quenched at the desired endpoint.

As described above, inorganic or polymer layers may be used to control the gap between two metal layers of a multi-layered metal core. For instance, chemically resistant $SiO_2$ layers that are just 2-3 nm in thickness have been fabricated over a metal core. Deposition of another metal layer over these shells will both push the plasmon response further into the NIR, and create a well-defined gap between the two metal layers of the core, similar to the creation of nanoparticle aggregates. By embedding a Raman reporter within this layer, a major increase in electromagnetic enhancement is expected. Dielectric spacer thickness has even more impact on the plasmon response of the overall enhancing core, so ideally the dielectric layers will be grown and etched with 1 nm precision. Likely candidates for dielectric spacer development are layers of polymer with alternating charge. Such layer-by-layer (LBL) deposition strategies should allow for sub-nanometer control of layer thickness A major advantage of a nanoparticle having a core comprised of one or more layers is that the growth template may be selectively removed. $SiO_2$ growth-template layers can be removed with HF etching, and the subsequent void replaced with reporter molecule or other lower density materials to enhance the ability of these particles to remain suspended in a liquid matrix. Use of mixed Au/Ag layers (or other alloys) also allows the preparation of perforated layers within the multi-layer core by selective Ag etching, facilitating template removal/replacement. Likewise, the formation of Au nanoparticles has been demonstrated on the inner surface of an otherwise hollow silica layer, which may be followed by insertion of Raman-active materials. It is possible to expand on this method, and allow large excesses of reporter to diffuse within the silica layer, followed by further metal growth to seal the reporter inside. The possible inclusion of a hollow SES enhancing inner layer within the multi-layered core could further enhance SERS response at eye-safe wavelengths.

F. Aggregations of Smaller Particles

In addition to the direct creation of SES enhancing core constructs that possess ideal electromagnetic properties, the overall performance of a SES active particle may be affected by controlling the aggregation, or assembly of isotropic or anisotropic particles. For example, dramatic differences have been shown in the extinction profiles between gold nanorods that are aligned end-to-end versus side-by-side.

Thus, it may be possible to use aggregates of small particles and obtain a SERS response with an excitation wavelength of about 1550 nm. For example, finite-element method simulations show that it is possible to create an aggregate of small Au nanoparticles that is resonant in the IR. Simulations performed with the COMSOL Multiphysics 3.4 software package show that an aggregate of five 20-nm diameter Au colloid can have a plasmon resonance at about 1450 nm, as shown in the graphs of FIG. 8. The simulation assumes that the nanoparticles would be in physical contact and arranged in a linear configuration that was parallel to the polarization of the incoming light. Under these conditions, the plasmon resonance of this structure is shifted to wavelengths much longer than the 520-nm plasmon resonance of the individual particles. It is also demonstrated that such aggregates would be effective for SERS at long wavelengths since they create high electromagnetic near field enhancements at their plasmon resonance.

The development of new core designs as described above may address the concerns of plasmonics that are useful at longer, eye-safe wavelengths, but these core designs may not be conducive to use with SES active particles that are required to remain suspended in a liquid for an extended period of time. Organic materials may be attached, deposited or grown upon the outside of the described particles to improve the ability of these particles to remain suspended in a liquid.

Au and Ag are the predominantly discussed metals for SES active particle cores. Au and Ag have traditionally received the most attention because the plasmon response of these materials matches well with standard red excitation wavelengths and these materials are reasonably stable. Alternative materials such as Cu, should possess excellent plasmonic properties for excitation at longer, eye-safe wavelengths, but CU is very prone to oxidation. In addition, other SES enhancing materials exist which may be used to anisotropic enhancing cores, including but not limited to Pd, Pt, Co and similar metals. These alternative core materials might possess interesting extinction profiles in the NIR, or be useful templates for additional coatings.

SERS Active Reporters Suitable for Use with Eye-Safe Excitation Wavelengths

The suitability of a SES active particle for effective excitation at eyesafe wavelengths may also be determined by the SES active reporter chosen, or a combination of the reporter and enhancing core configuration. For example, resonant reporters suitable for particles that may be excited at eye-safe wavelengths may be based on transition metal complexes, where three types of reporter-centered resonance are possible at about 1550 nm. First, it is known that transition octahedral metal $d^8$ complexes (e.g. $Ni^{2+}$ salts) exhibit easily-measurable absorbances in the near-IR emanating from $^3A_{2g} \rightarrow {}^3T_{2g}$ optical transitions. Because these transitions are between d orbitals, they are symmetry-disallowed and therefore weak, with typical molar absorptivities (∈) in the 0.5-50 $M^{-1}cm^{-1}$ range. Nevertheless, they are attractive synthetic targets, insofar as they can be very stable. For example, by use of $NH_3$ as a ligand the use of carbon can be avoided. Likewise, they can be made to adsorb to a SERS enhancing metal core by using simple charge considerations.

Alternatively, metal-to-ligand-charge transfer (MLCT) optical transitions, or the converse LMCT transitions, where in both cases electron density is partly delocalized between metal and ligand molecular orbitals, are also known in transition metal chemistry (an example of the former being [Ru (bpy)$_3$]$^{2+}$). These transitions involve orbitals of gerade (M) and ungerade (L) symmetry and are therefore allowed, and can have ∈ values in the 5,000-50,000 $M^{-1}cm^{-1}$ range. In transition metal complexes, these transitions are typically in the visible range of wavelengths. MLCT or LMCT transitions between reporters and enhancing cores may be found near 1550 nm. Evidence of this has been demonstrated as described below at 1064 nm, where the reporter AZP shows anomalously intense SERS spectra compared to other reporters, as evidenced by the relative ratios SERS intensities at 785 nm 1064 nm, which would have been expected to follow the relationship of approximately [1064/785]$^4$.

Figure 9A:
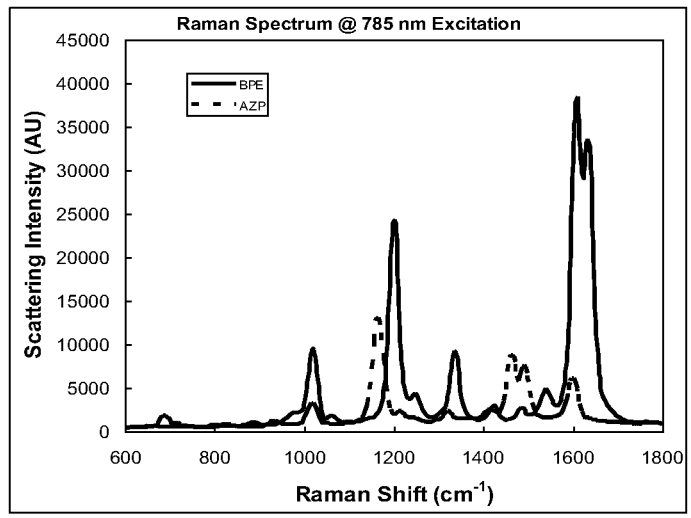
FIG. 9 is a graphic representation of the SERS spectra of a nanotag using an AZP reporter molecule when excited at 785 nm (FIG. 9A), 1064 nm (FIG. 9B), and 1546 nm (FIG. 9C).
Figure 9B:
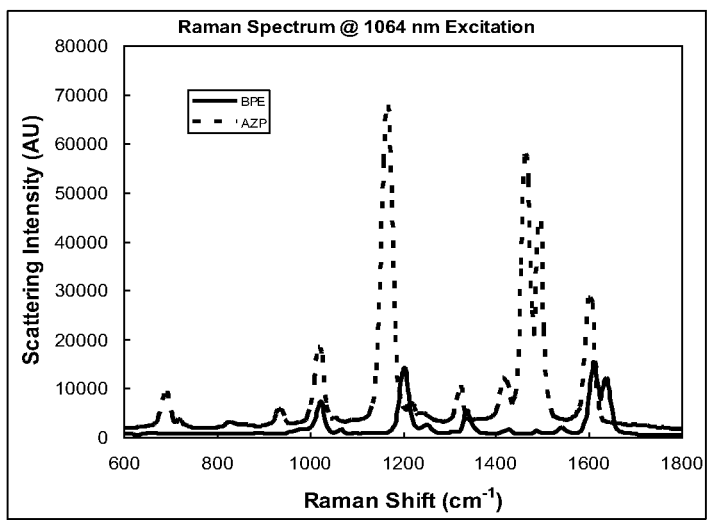
Figure 9C:
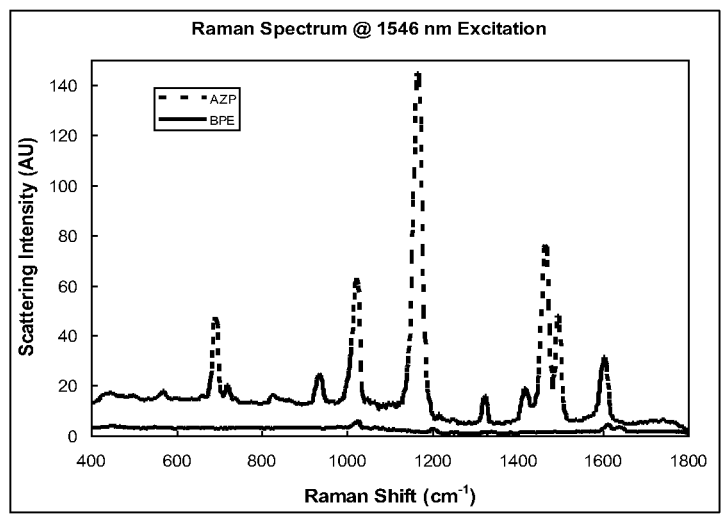

In particular, FIGS. 9A, 9B and 9C show the SERS spectra of 4,4'azopyridine (AZP) and 1,2-bis(4-pyridyl)ethylene (BPE) SERS nanotags at 3 different excitation wavelengths: 785 nm, 1064 nm and 1546 nm Both types of SERS nanotags have 90 nm gold cores. AZP and BPE have very similar molecular structure, as shown below, including the same size of conjugated path and same binding groups to metal.

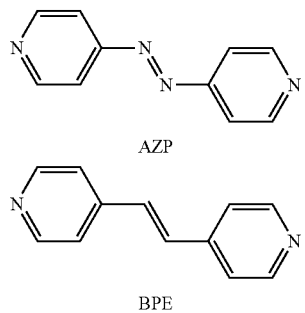

The obvious difference between the two reporter molecules is the nature of the group bridging the aromatic rings, which results in different energy levels of their HOMO and LUMO orbitals, as it is demonstrated by the different color of these compounds. The unusually high enhancement for AZP tags at longer wavelengths, as shown by comparing the scattering intensity graphed in FIG. 9A, corresponding to 785 nm excitation and 9B, corresponding to 1064 nm excitation with 9C corresponding to 1546 nm excitation may be due to the metal-to-ligand or ligand-to-metal charge transfer between AZP and the metal, made possible by its characteristic molecular orbital energies.

Other aromatic azo type compounds that may be equally efficient as reporter molecules at eyesafe wavelengths include but are not limited to 4,4'-diethynylazobenzene, 4-(4-quinolylazo)pyridine, 4-(4-ethynylphenylazo)pyridine, 5-(4-pyridylazo)imidazole, 3-(4-pyridylazo)thiophene, 5-(4-pyridylazo)thiazole and similar compounds.

A third interesting transition metal complex includes mixed-valence or intervalence transfer (IT) complexes, which exhibit very intense, broad absorbances in the near-IR/ IR region of the spectrum. These absorbances result from electrons being shared across two or more metals bridged by an organic ligand like —CN or pyrazine. This smearing of electron density leads to high polarizabilty, a key factor for Raman emission. Simple examples of mixed-valence compounds include the classic Creutz-Taube ion, for which a resonance Raman spectrum in solution using 1320 nm excitation has been published and the even simpler Prussian Blue.

Figure 10:
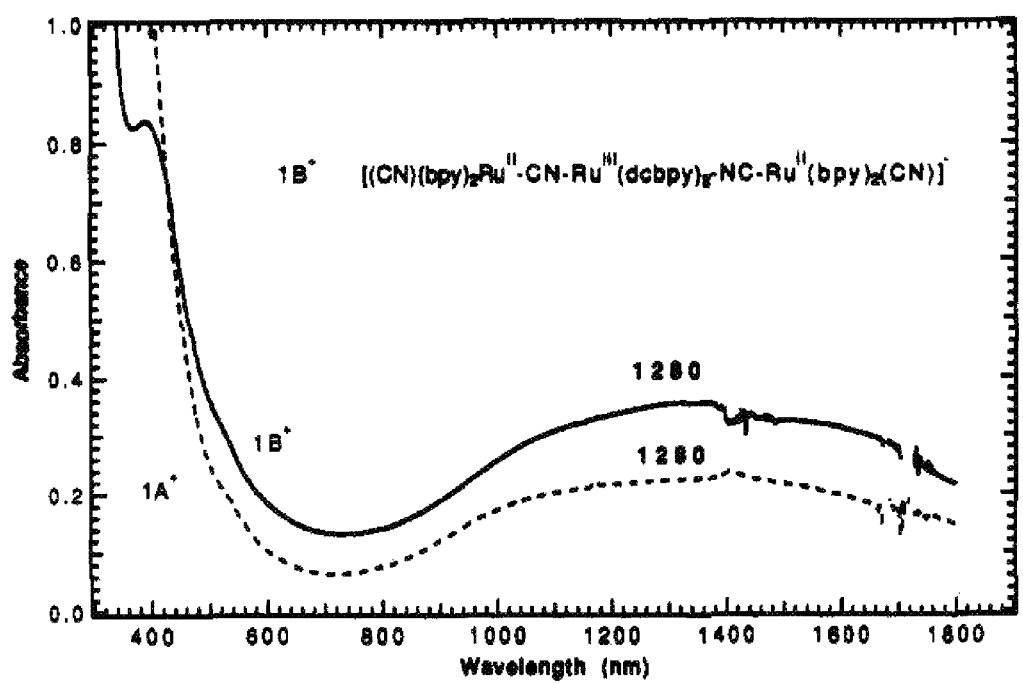
FIG. 10 is a graphic representation of the absorbance spectrum of a selected mixed-valence transition metal reporter.

A series of mixed-valence transition metal compounds with intense IT bands in the near IR may be suitable for reporters in SES tags useful at eyesafe wavelengths. These include complexes containing 2-6 Ru, Os, or Fe metal ions, with ligands chosen so that they will adsorb to the enhancing metal core surfaces. For example, the trinuclear anion[(CN)(bpy)$_2$Ru—CN—Ru(dcbpy)$_2$—NC—Ru(bpy)$_2$(CN)]$^-$ (where bpy=2,2'-bipyridine and dcbpy=4,4'-dicarboxy-2,2'-bipyridine) may be made, having the optical spectrum shown in FIG. 10. This molecule has an ∈ at $\lambda_{max}$ (1280 nm) of 4600 $M^{-1}cm^{-1}$ that clearly extends out beyond 1500 nm, and has four free carboxylates that can be used to anchor it to metal surfaces.

A series of mixed-valent, olefin-linked ferrocenes that exhibit ∈ at $\lambda_{max}$ between 1500 and 1800 nm of approximately 2000 $M^{-1}cm^{-1}$, introducing —SH or —$NH_2$ groups to induce binding to an enhancing metal core may also be made. Alternatively, mixed-valence complexes of the general structure shown below are described in (*Angew. Chem. Int. Ed.* 2007, 46, 1778-1796 and references therein), which include species formed by 2 or more metal atoms where $M^{II}$ and $M^{III}$ are Ru, Os or Fe in oxidation state +2 and +3 respectively, BL is a conjugated bridge ligand that includes pyrazine, 4,4'bipyridyl, 1,2-bis(4-pyridyl)ethylene, 1,4-bis(4-pyridyl)benzene, 1,4-bis-[(4-pyridyl)ethenyl]benzene, acetylene, diacetylene, triacetylene, tetracetylene, 1,2-diethynylbenzene, 4,4'-diethynyl-biphenyl, 4,4"diethynyl-p-terphenyl, 4-ethynylpyridine, 4-(4-ethynylphenyl)pyridine, 1-(4-pyridyl)-2-(4-ethynylphenyl)ethylene or similar compounds. $L_n$ are mono- or multi-dentate ligands that complete the coordination sphere of the metal and contain functional groups that may bind to the metal core, including 2,2'-dipyridyl, 2,2'-bipyridine-4,4'-dicarboxylic acid, 2,2':6',2"-terpyridine, 1,10-phenanthrolin-5-amine, and similar compounds.

As described above, SERS tags that may be excited at relatively long, eyesafe wavelengths are useful since the laser devices used to detect such tags are exceptionally safe. There also exists a strong commercial market for instrumentation to enhance night vision. Such instrumentation can range in complexity from handheld apparatus, for example night vision binoculars, to more elaborate instrumentation that is mounted in a stationary position or even on a moving vehicle for many uses, including but not limited to night-time battle. In all cases, these instruments use near-IR detection in the form of a heat differential between objects or locations. The particles described herein that emit SERS signatures at longer infrared wavelengths may be detected by instruments for SERS-based night vision or hybrid instruments that detect both heat and SERS signatures.

An alternative embodiment includes a method of manufacturing a particle as described above which particle produces a measurable SES spectrum when excited by incident light having a wavelength of at least 1400 nm.

An alternative embodiment includes a detection system comprising a particle as described above and a detector having an illumination source providing illumination at a wavelength of at least 1400 nm.

An alternative embodiment includes a method of tagging a material comprising providing a particle as described above which has a measurable SES spectrum when excited by incident light having a wavelength of at least 1400 nm and associating the particle with a material of interest. For example, the small, robust, non-toxic, and easily-attachable nature of the eye-safe particles disclosed herein allows their use for tagging virtually any desired object. The tracked object can be made of solid, liquid, or gas phase material or any combination of phases. The material can be a discrete solid object, such as a container, pill, or piece of jewelry, or a continuous or granular material, such as paint, ink, fuel, or extended piece of, e.g., textile, paper, or plastic, in which case the particles are typically distributed throughout the material.

Examples of specific materials or objects that can be tagged with the eye-safe particles disclosed herein, or into which the particles can be incorporated include, but are not limited to:

Packaging, including adhesives, paper, plastics, labels, and seals

Agrochemicals, seeds, and crops

Artwork

Computer chips

Cosmetics and perfumes

Compact disks (CDs), digital video disks (DVDs), and videotapes

Documents, money, and other paper products (e.g., labels, passports, stock certificates)

Inks, paints, varnishes, lacquers, overcoats, topcoats, and dyes

Electronic devices

Explosives and weapons

Food and beverages, tobacco

Textiles, clothing, footwear, designer products, and apparel labels

Polymers

Insects, birds, reptiles, and mammals

Powders

Luxury goods

Other anti-counterfeiting substances or materials, such as holograms, optically variable devices, color-shifting inks, threads, and optically-active particles Hazardous waste Movie props and memorabilia, sports memorabilia and apparel Manufacturing parts, automobile parts, aircraft parts, truck parts Petroleum, fuel, lubricants, gasoline, crude oil, diesel fuel, fuel additive packages, crude oil Pharmaceuticals, prescription drugs, over-the-counter medicines, and vaccines The eye-safe particles disclosed herein can be associated with the material in any way that maintains their association, at least until the particles are read. Depending upon the material to be tagged, the particles can be incorporated during production or associated with a finished product. Because they are so small, the particles are unlikely to have a detrimental effect on either the manufacturing process or the finished product. The particles can be associated with or attached to the material via any chemical or physical means that does not inherently interfere with particle functionality. For example, particles can be mixed with and distributed throughout a liquid-based substance such as paint, oil, or ink and then applied to a surface. They can be wound within fibers of a textile, paper, or other fibrous or woven product, or trapped between layers of a multi-layer label. The particles can be incorporated during production of a polymeric or slurried material and bound during polymerization or drying of the material. Additionally, the surfaces of the particles can be chemically derivatized with functional groups of any desired characteristic, for covalent or non-covalent attachment to the material. When the particles are applied to a finished product, they can be applied manually by, e.g., a pipette, or automatically by a pipette, spray nozzle, or the like. Particles can be applied in solution in a suitable solvent (e.g., ethanol), which then evaporates.

The eye-safe particles disclosed herein have a number of inherent properties that are advantageous for tagging and tracking applications. They offer a very large number of possible codes. For example, if a panel of particles is constructed with 20 distinguishable Raman spectra, and an object is labeled with two particles, there are 20*19/2=190 different codes. If the number of particles per object is increased to 5, there are 15,504 possible codes. Ten particles per object yields $1.1 \times 10^6$ different codes. A more sophisticated monochromator increases the number of distinguishable spectra to, e.g., 50, greatly increasing the number of possible codes. Alternatively, different amounts of particles can be used to generate an exponentially-increased number of possible codes. For example, with just four different particle types (N=4), present at three different intensity levels (e.g. High, Medium, Low) (L=3), chosen three at a time (P=3), can generate 58 different codes. With N=10, P=3, L=1, the number of codes is 175. With N=50, P=5, L=4, over a billion codes are possible.

In some embodiments, the particles may be applied to a document or other item in an ink or other marking material. Inks include, but are not limited to flexographic ink, lithographic ink, silkscreen ink, gravure ink, bleeding ink, coin reactive ink, erasable ink, pen reactive ink, heat reactive ink, visible infrared ink, optically variable ink, and penetrating ink, photochromic ink, solvent/chemical reactive ink, thermochromic ink, and water fugitive ink. A PSP may also be applied in electrophotographic and ink jet printing machines and other systems including offset lithography, letterpress, gravure, heliogravure, xerography, photography, silk-screening systems, systems for imagewise deposition of discrete quantities of a marking material on a substrate surface, such as paint, chemical, and film deposition systems; and systems for integration of colorant materials in an exposed surface of a fibrous substrate, such as textile printing systems.

It should be noted that additional security features may be included or utilized along with the disclosed tags for a particular item or documents. One such additional security feature may be a separate security ink, such as bleeding ink, coin reactive ink, erasable ink, pen reactive ink, heat reactive ink, visible infrared ink, optically variable ink, penetrating ink. photochromic ink, solvent/chemical reactive ink, thermochromic ink or water fugitive ink. The tags may be applied as part of the ink, or in a separate step. Other non-ink based security features which may be utilized in addition to the disclosed tags for document or item marking include the use of an ascending serial number (horizontal and/or vertical format), bar code and numerals, colored fibers, embedded security thread, face-back optical registration design (transparent register), foil imprints, holograms, latent impressions, micro printing, optical variable devices (OVD), planchettes, raised marks, segmented security threads, and watermarks.

The disclosed particles may be applied by coating an image, including but not limited to a hologram image, made with toner or ink compositions known in the art, as with an overcoat varnish, or a starch overcoat.

In the case of documents with other security features, such as those including polymer threads or metal foils, the particles may be applied to additional feature, such as the thread or the foil. Single tags may be considered to represent a bit of data that may be changeable according to the methods described herein. Thus groups of distinguishable eye-safe particles disclosed herein may be applied to constitute an "alphabet" and combined as words or encoded information, which may be selectively variable, or variable over time.

Typically, if a suitable waveguide (e.g., optical fiber) is provided for transmitting light to and from the object, the excitation source and detector can be physically remote from the object being verified. This allows the disclosed particles to be used in locations in which it is difficult to place conventional light sources or detectors. The nature of Raman scattering and laser-based monochromatic excitation is such that it is not necessary to place the excitation source in close proximity to the Raman-active species. Moreover, the eye-safe particles disclosed herein are amenable for use with all known forms of Raman spectrometers, including some more recent implementations, including spatially offset Raman, Raman absorption spectrometers, instruments to measure Raman optical activity, and so forth provided these devices are configured to emit light at a suitably long wavelength.

Another characteristic of eye-safe particles is that the measurement of their spectra does not need to be strictly confined to "line of sight" detection, as with, e.g., fluorescent tags. Thus their spectrum can be acquired without removing the particles from the tagged object, provided that the material is partially transparent to both the excitation wavelength and the Raman photon. For example, water has negligible Raman activity and does not absorb visible radiation, allowing the particles disclosed herein in water to be detected. The eye-safe particles can also be detected when embedded in, e.g., clear plastic, paper, or certain inks.

The disclosed particles also allow for quantitative verification, because the signal intensity is an approximately linear function of the number of analyte molecules. For standardized particles (uniform analyte distribution), the measured signal intensity reflects the number or density of particles. If the particles are added at a known concentration, the measured signal intensity can be used to detect undesired dilution of liquid or granular materials.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments disclosed herein have been particularly shown and described with reference to a number of examples, it would be understood by those skilled in the art that changes in the form and details may be made to the various embodiments disclosed herein without departing from the spirit and scope of the disclosure and that the various embodiments disclosed herein are not intended to act as limitations on the scope of the claims.

All references sited herein are incorporated in their entirety by reference for all matters disclosed therein.

What is claimed is:

1. A particle comprising:
    a hollow surface-enhanced spectroscopy (SES)-active core comprising;
        a hollow metal inner layer;
        a dielectric layer formed over the exterior of the hollow inner layer; and
        a metal outer layer formed over the exterior of the dielectric layer;
    a SES-active reporter molecule doped within the dielectric layer of said SES-active core wherein the SES-active reporter molecule comprises at least one of 4,4'-azopyridine, 4,4'-diethynylazobenzene, 4-(4-quinolylazo)pyridine, 4-(4-ethynylphenylazo)pyridine, 5-(4-pyridylazo)imidazole and 3-(4-pyridylazo)thiophene, 5-(4-pyridylazo)thiazole, and wherein said particle has a measurable SES spectrum when excited by incident light having a wavelength of at least 1400 nm.

2. The particle of claim 1 wherein the SES active core supports plasmon resonance at a wavelength of at least 1400 nm.

3. The particle of claim 2 wherein the SES active core comprises an anisotropic core.

4. The particle of claim 2 wherein the hollow metal inner layer of the SES active core comprises a hollow sphere.

5. The particle of claim 1 wherein the SES-active reporter molecule is resonant at one or more wavelengths greater than or equal to 1400 nm.

* * * * *